United States Patent [19]

Cella et al.

[11] 4,272,544

[45] Jun. 9, 1981

[54] SKIN CELL RENEWAL REGIME

[75] Inventors: John A. Cella, Carmel; Merlyn G. Flom, Noblesville; Anne M. Herrold, Brownsburg; Joe O. Martin, Martinsville; Ovidio Vargas, Carmel, all of Ind.

[73] Assignee: Eli Lilly and Company, Indianapolis, Ind.

[21] Appl. No.: 179,627

[22] Filed: Aug. 20, 1980

[51] Int. Cl.³ ............................................. A61K 31/415
[52] U.S. Cl. ................................. 424/273 R; 424/83; 424/358; 424/365
[58] Field of Search ...................... 424/83, 358, 273 R, 424/365

[56] References Cited

U.S. PATENT DOCUMENTS

| 3,196,079 | 7/1965 | Herrold et al. | 424/83 |
| 4,164,564 | 8/1979 | Chen | 424/83 |
| 4,216,201 | 8/1980 | Calvo | 424/63 |

OTHER PUBLICATIONS

Leszczynska-Bakal, et al., Dissert. Pharm. Pharmacol., 1970, vol. 22, No. 1, pp. 56-60.
A-C Polyethylene Bulletin, (5011-22-1A), 7/14/1977.
A-C Polyethylene Bulletin (5011-24-2), 8/16/1977.
A-C Polyethylene Bulletin (5189-4-4), 8/8/1978.

Primary Examiner—Dale R. Ore
Attorney, Agent, or Firm—Karen B. O'Connor; Arthur R. Whale

[57] ABSTRACT

A novel cell renewal cosmetic regime is disclosed, which increases epidermal cell turnover without skin irritation. The regime consists of the use of four components: a cleanser, a cream, a lotion, and a tonic.

2 Claims, No Drawings

SKIN CELL RENEWAL REGIME

BACKGROUND OF THE INVENTION

This invention relates to a novel cell renewal cosmetic regime, which increases the rate of cell turnover without skin irritation.

In the natural renewing cycle of skin, cells are constantly being born, rising through the epidermal layers to the surface and falling off. A young skin renews its surface layers every two to three weeks. A mature skin can take twice as long. And the longer this process takes, the more cells develop areas of weakness that cause a faster loss of natural moisture and the dry lifeless appearance that's found in older-looking skin.

Acceleration of natural cell renewal or turnover speeds the replacement of dead cells by new ones in the outer epidermal layer or stratum corneum, thereby giving the skin a younger-looking appearance. The newer cells are moist and fresh, replacing the old, dry cells on the surface.

Although irritation of the skin will increase the sloughing off of dead stratum corneum cells, such irritation is undesirable because of the damage to the skin. It is, therefore, desirable to increase cell turnover without irritation.

SUMMARY OF THE INVENTION

It is, therefore, an object of the present invention to provide a method of increasing the rate of skin cell turnover without causing irritation, using a regime, which consists of the application to the skin of four components. The four components are: a cleanser, a cream, a lotion, and a tonic.

DESCRIPTION OF THE PREFERRED EMBODIMENTS

In accordance with this invention there is provided a method of increasing the rate of cell turnover without causing skin irritation, which comprises applying to the skin in a prescribed regime a cleanser, a cream, a lotion, and a tonic. Each of the four components is a separate invention; the cleanser is claimed in Application Ser. No. 179,628, filed of even date herewith; the cream is claimed in Application Ser. No. 179,626, also filed of even date herewith, the lotion is claimed in Application Ser. No. 179,629, filed of even date herewith; and the tonic is claimed in Application Ser. No. 179,625, filed of even date herewith.

The preferred regime usually begins in the morning with the use of the tonic, followed by the lotion. Later, usually at night, the cleanser is used and then the tonic and cream are applied. However, the order and the timing of the use of the four products can be varied to suit individual needs. For example, the cleanser can also be used in the morning. Some effect will be obtained even if all the compositions are not used or if there is a delay between usage.

The cleanser formulation consists essentially of, in percent by weight:

| Ingredients | Percent |
| --- | --- |
| deionized water | 39.73 |
| propylene glycol | 6.00 |
| magnesium aluminum silicate | 1.10 |
| sodium carboxymethyl cellulose | 0.10 |
| methyl p-hydroxybenzoate | 0.20 |
| imidazolidinyl urea | 0.30 |
| ethylenediaminetetraacetic acid | 0.02 |
| sodium N-lauryl-$\beta$-iminodipropionate | 4.00 |
| titanium dioxide | 0.75 |
| sodium isostearoyl-2-lactylate | 2.00 |
| soya sterols | 1.00 |
| polyoxyethylene (10) soya sterols | 2.50 |
| polyoxyethylene (3) myristyl ether myristate | 8.00 |
| polyoxypropylene (15) stearyl ether | 8.00 |
| heavy mineral oil | 8.00 |
| propylene glycol dicaprylate/dicaprate (80/20 to 50/50) | 7.00 |
| cetyl alcohol (1-hexadecanol) | 4.00 |
| stearyl alcohol (1-octadecanol) | 2.00 |
| propyl p-hydroxybenzoate | 0.10 |
| glyceryl monostearate and polyethylene glycol (100) monostearate | 2.00 |
| triple pressed stearic acid | 2.50 |
| lactic acid | 0.10 |
| fragrance | 0.60 |

The cream formulation consists essentially of, in percent by weight:

| Ingredients | Percent |
| --- | --- |
| light mineral oil | 4.45 |
| polyethylene homopolymer (1500 m. wt., density 0.91 g/cc) | 2.50 |
| undecanoic triglyceride | 2.00 |
| squalane | 5.00 |
| distilled lanolin alcohol | 0.55 |
| white beeswax | 1.00 |
| polydimethyl cyclosiloxane | 9.00 |
| triglyceryl diisostearate | 4.00 |
| isopropyl myristate | 5.00 |
| propyl p-hydroxybenzoate | 0.10 |
| quaternary bentonite | 0.40 |
| deionized water | 59.00 |
| methyl p-hydroxybenzoate | 0.20 |
| 70% sorbitol solution | 5.00 |
| imidazolidinyl urea | 0.30 |
| urea | 0.50 |
| glyoxyldiureide | 0.20 |
| DL-pantothenyl alcohol | 0.50 |
| cis-1-(3-chloroallyl)-3,5,7-triaza-1-azoniaadamantane chloride | 0.10 |
| fragrance | 0.20 |

The lotion formulation consists essentially of, in percent by weight:

| Ingredients | Percent |
| --- | --- |
| deionized water | 69.35 |
| xanthan gum | 0.15 |
| propylene glycol | 5.00 |
| polyoxyethylene (30) stearate | 1.70 |
| methyl p-hydroxybenzoate | 0.20 |
| imidazolidinyl urea | 0.30 |
| polyphenylmethylsiloxane | 3.00 |
| polyethylene homopolymer (1500 m. wt., density 0.91 g/cc) | 1.00 |
| glyceryl monostearate, neutral non-emulsifying | 2.00 |
| propyl p-hydroxybenzoate | 0.20 |
| sorbitan monostearate | 2.00 |
| ethylene glycol monostearate | 1.00 |
| lanolin oil | 2.50 |
| isopropyl myristate | 3.00 |
| squalane | 8.50 |
| fragrance | 0.10 |

The tonic formulation consists essentially of, in percent by weight:

| Ingredients | Percent |
| --- | --- |
| deionized water | 80.12 |
| polyethylene and polypropylene glycol | 2.00 |
| glyoxyldiureide | 0.20 |
| polyethylene glycol 300 | 9.00 |
| imidazolidinyl urea | 0.40 |
| denatured alcohol | 7.00 |
| methyl p-hydroxybenzoate | 0.10 |
| propyl p-hydroxybenzoate | 0.05 |
| polyoxyethylene sorbitan fatty acid ester | 0.30 |
| ethoxylated oleyl alcohol | 0.50 |
| menthol | 0.03 |
| fragrance | 0.30 |

In general, the individual ingredients used in the formulations should be of a quality or purity (such as U.S.P. or N.F.) suitable for cosmetic use.

The formulations are prepared by mixing the ingredients according to conventional methods. The preparation of these formulations is described in the following examples. The examples are illustrative of the formulations, but are not to be construed as limiting the invention.

EXAMPLE 1

Cleanser

Formulation:

| Phase | Ingredient | Percent by weight |
| --- | --- | --- |
| A | Deriphat 160C (Velvetex 610-L, Henkel, sodium N-lauryl-&-iminodipropionate) | 4.00 |
|  | titanium dioxide, atlas white | 0.75 |
| B | Veegum K (R. T. Vanderbilt, magnesium aluminum silicate) | 1.10 |
|  | Sodium CMC-7MF (Hercules, sodium carboxymethyl cellulose) | 0.10 |
| C | propylene glycol | 6.00 |
| D | deionized water | 39.73 |
| E | methylparaben (methyl p-hydroxybenzoate) | 0.20 |
|  | imidazolidinyl urea | 0.30 |
|  | EDTA (ethylenediaminetetraacetic acid) | 0.02 |
| F | Pationic ISL (Patco Products, sodium isostearoyl-2-lactylate) | 2.00 |
|  | soya sterol | 1.00 |
|  | POE (10) soya sterol (polyoxyethylene (10) soya sterols) | 2.50 |
|  | Standamul 1414E (Henkel, polyoxyethylene (3) myristyl ether myristate) | 8.00 |
|  | POP (15) stearyl ether (polyoxypropylene (15) stearyl ether) | 8.00 |
|  | heavy mineral oil | 8.00 |
|  | propylene glycol dicaprylate/dicaprate (50/50) | 7.00 |
|  | cetyl alcohol (1-hexadecanol) | 4.00 |
|  | stearyl alcohol (1-octadecanol) | 2.00 |
|  | propylparaben (propyl p-hydroxybenzoate) | 0.10 |
|  | Arlacel 165 (ICI, glyceryl monostearate and polyethylene glycol (100) monostearate) | 2.00 |
|  | triple pressed stearic acid | 2.50 |
| G | lactic acid | 0.10 |
| H | Essence 66.001 (Firmenich, fragrance) | 0.60 |

Procedure:

Phase A is prepared one day before the rest of the batch by adding the titanium dioxide to the Deriphat 160C with constant mixing by a Lightnin' mixer. Mixing is continued until a uniform mass is obtained and the titanium dioxide is completely wetted. Phase A is aged overnight at room temperature.

A dry blend of the Phase B ingredients is prepared separately from Phase A the next day. Phase B is then slowly added to Phase C, while mixing vigorously with a Lightnin' mixer. Phase BC is mixed continuously and then added to Phase D. Phase BCD is mixed with a sweep agitator until all the gum is dispersed.

The ingredients of Phase E are added one at a time to Phase BCD and mixed until all the powders are dissolved. Phase A is remixed thoroughly with a Lightnin' mixer until uniform. Phase A is added to Phase BCDE, while mixing with sweep and side agitator for about 5 to 10 minutes. Afterwards Phase ABCDE is heated to about 80°–85° C. with continued mixing.

Phase F is prepared in a separate container and heated to about 90°–95° C. Mixing and heating are continued until the soya sterols are melted and the mixture is uniform. Phase F is then added to Phase ABCDE and mixed thoroughly.

Phase ABCDEF is then cooled to 60°–65° C. with continuous mixing, and then Phase G is added. Everything is then mixed thoroughly with the side-sweep. Phase ABCDEFG is cooled to about 45°–50° C., and then Phase H is added. The side-sweep is used to mix the phases, while the entire mixture is allowed to cool to room temperature. Mixing is continued with the side-sweep for about 15–20 minutes and the mixture is transferred into suitable stainless steel containers.

EXAMPLE 2

Cream

Formulation:

| Phase | Ingredient | Percent by weight |
| --- | --- | --- |
| A | light mineral oil | 4.45 |
|  | Polyethylene 617 (Allied Chemical, polyethylene homopolymer, 1500 m. wt., density 0.91 g/cc, softening pt. 102° C., viscosity at 140° C. 145 cps) | 2.50 |
| B | glyceryl triundecanoate (undecanoic triglyceride) | 2.00 |
|  | Robane (Robeco, squalane) | 5.00 |
|  | Super Hartolan (Croda, distilled lanolin alcohol) | 0.55 |
|  | white beeswax | 1.00 |
|  | Silicone Fluid 344 (Dow Corning, polydimethyl cyclosiloxane) | 9.00 |
|  | triglyceryl diisostearate (polyglyceryl-3-diisostearate) | 4.00 |
|  | isopropyl myristate | 5.00 |
|  | propylparaben(propyl p-hydroxybenzoate) | 0.10 |
| C | Bentone No. 38(NL Industries, quaternary bentonite) | 0.40 |
| D | deionized water | 58.00 |
|  | methylparaben (methyl p-hydroxybenzoate) | 0.20 |
|  | sorbitol solution 70% (U.S.P. Sorbo) | 5.00 |
|  | imidazolidinyl urea | 0.30 |
|  | urea | 0.50 |
|  | Allantoin (Sutton and Schuylkill, glyoxyldiureide) | 0.20 |
|  | dL-Panthenol (DL-pantothenyl alcohol) | 0.50 |
| E | Dowicil 200 (Dow Chemical, cis isomer of 1-(3-chloroallyl)-3,5,7-triaza-1-azoniaadamantane chloride) | 0.10 |
|  | deionized water | 1.00 |
| F | Essence 66.001 (Firmenich, fragrance) | 0.20 |

Procedure:

The light mineral oil of Phase A is heated to about 90°–95° C. and then the polyethylene is added while mixing with a Lightnin' mixer. The mixing is continued until Phase A becomes a clear solution. The ingredients of Phase B are added to a jacketed tank that is equipped with a homomixer and a side-sweep. (Ross) Phase B is heated to about 90°–95° C. and mixed thoroughly. Phase A is added to Phase B and then mixed thoroughly with the homomixer.

While Phase AB is being mixed with the homomixer, the Bentone of Phase C is slowly sprinkled into Phase AB. Mixing is continued until the Bentone is completely wetted and a homogeneous mass is acquired. The temperature is maintained at 90°–95° C.

The ingredients of Phase D are added to a container equipped with a Lightnin' mixer. The container is then heated to about 90°–95° C. and Phase D is mixed until the powder ingredients are dissolved. Phase D is added to Phase ABC and mixed with the homomixer and side-sweep. The product is homomixed until it becomes homogeneous and has a bright white shine. Homomixing is stopped when the product has cooled to 50° C., but side-sweeping continues. The product is then cooled, but must not be shock cooled.

Phase E is prepared separately by dissolving the Dowicil 200 in the deionized water. Phase ABCD is cooled to about 40°–45° C. and Phase E is added. The product is mixed thoroughly with the side-sweep. Phase F is added, keeping the mixture at about 40°–45° C. and mixing completely. The product is then discharged into suitable stainless steel storage containers.

EXAMPLE 3

Lotion

Formulation:

| Phase | Ingredient | Percent by weight |
|---|---|---|
| A | deionized water | 69.35 |
|  | Keltrol (Kelco, xanthan gum) | 0.15 |
|  | propylene glycol | 5.00 |
|  | POE (30) stearate (polyoxyethylene (30) stearate) | 1.70 |
|  | methylparaben (methyl p-hydroxybenzoate) | 0.20 |
|  | imidazolidinyl urea | 0.30 |
|  | Silicone Antifoam 72(G.E., Silicone Division, polyphenylmethylsiloxane) | 3.00 |
| B | Polyethylene 617 (Allied Chemical, polyethylene homopolymer, 1500 m. wt., density 0.91 g/cc, softening pt. 102° C., viscosity at 140° C. 145 cps) | 1.00 |
|  | Cerasynt SD (Van Dyk and Co., neutral, non-emulsifying glyceryl monostearate) | 2.00 |
|  | propylparaben (propyl p-hydroxybenzoate) | 0.20 |
|  | sorbitan monostearate | 2.00 |
|  | EGMS (ethylene glycol monostearate) | 1.00 |
|  | lanolin oil | 2.50 |
|  | isopropyl myristate | 3.00 |
|  | Robane (Robeco, squalane) | 8.50 |
| C | Essence 66.001 (Firmenich, fragrance) | 0.10 |

Procedure:

The ingredients of Phase A are heated to about 80°–85° C. and mixed with a Lightnin' mixer until the Keltrol is completely hydrated. The ingredients of Phase B are heated to about 85°–90° C. and then mixed with a Lightnin' mixer until the polyethylene is completely dissolved. Phase B is added to Phase A with mixing and the temperature of Phase AB is maintained at about 75°–80° C. for ten minutes. The heat is removed and the mixture is cooled to 40° C. with continuing side-sweep mixing. Phase C is added and Phase ABC is mixed until homogeneous. The product is discharged by passing it once through a colloid mill. (Charlotte mill set at 0.010" gap setting and wide open discharge valve.) It is important to note that this product is shear sensitive, so excessive shear should be avoided.

EXAMPLE 4

Tonic

Formulation:

| Phase | Ingredient | Percent by weight |
|---|---|---|
| A | deionized water | 80.12 |
|  | UCON Lubricant 75H450 (Union Carbide, polyethylene and polypropylene glycol) | 2.00 |
|  | Allantoin (Sutton and Schuylkill, glyoxyldiureide) | 0.20 |
|  | PEG-300 (polyethylene glycol 300) | 9.00 |
|  | imidazolidinyl urea | 0.40 |
| B | SDA 40-2, 190 Proof (denatured alcohol) | 7.00 |
|  | methylparaben (methyl p-hydroxybenzoate) | 0.10 |
|  | propylparaben (propyl p-hydroxybenzoate) | 0.05 |
|  | Polysorbate 60 (ICI, polyoxyethylene sorbitan fatty acid ester) | 0.30 |
|  | POE (10) oleyl ether (ethoxylated oleyl alcohol) | 0.50 |
|  | menthol | 0.03 |
|  | Essence 66.001 (Firmenich, fragrance) | 0.30 |

Procedure:

The ingredients of Phase A are mixed with a Lightnin' mixer until the solution is clear. The ingredients of Phase B are then mixed in a separate container with a Lightnin' mixer until clear. Plase B is slowly added to Phase A with mixing. The product is filtered through a security type filter and is hazy after filtration. The product is then stored in a non-plastic container. All equipment and personnel should be grounded, since the formulation contains alcohol.

When the above-described formulations are used in accordance with the method of this invention, the rate of skin cell turnover is increased without skin irritation. The rate of skin cell turnover is frequently reported as transit time. Transit time is defined as the time required for a newly formed stratum corneum cell to rise up through the stratum corneum and finally slough off. Therefore, the less transit time required, the better the appearance of the skin, because younger cells are on its surface.

The test for measuring transit time is described by L. H. Jansen, et al., "Improved Fluorescence Staining Technique for Estimating Turnover of the Human Stratum Corneum," *British Journal of Dermatology*, 1974, 90, 9–12. The transit or replacement time of the human stratum corneum is determined by measuring the number of days required for a fluorescent marker, dansyl chloride, to disappear, after application to the skin. The dansyl chloride only stains the stratum corneum (outer cell layer) and the shedding of the stratum corneum is signified by the disappearance of the dansyl chloride.

Using the Jansen procedure, the transit time of the present regime is measured and compared with the transit time of several commercially available, skin-care cosmetic products, identified as products A to E in Table I. Dansyl chloride is applied to both upper inner arms of each subject, after two weeks of pretreatment with the product. Then one arm is treated daily with the particular product, while the other arm is untreated. The number of days required for the dansyl chloride to disappear from each arm is then recorded. The results for the treated arms are averaged for the particular product and compared to the average for the untreated arms. The results are shown in Table I. The larger the difference between the control and treated times, the more effective is the product.

The test was run using women from young (19–29 years) and middle (31–58 years) age groups for products A-E and the regime.

The present regime consists of using all four components in the following order: the cleanser and tonic were used in the morning, followed by the lotion; later, at night, the cleanser was used and then the tonic and cream were applied.

TABLE I

| Product | Number of Subjects | Mean Transit Time$^a$ Treated with Product | Mean Transit Time$^a$ Control (untreated) | Difference |
|---|---|---|---|---|
| A | 11 | 16.1 | 17.0 | 0.9 |
| B | 11 | 15.9 | 17.3 | 1.4 |
| C | 10 | 14.1 | 15.3 | 1.2 |
| D | 10 | 13.5 | 16.0 | 2.5 |
| E | 10 | 18.2 | 22.1 | 3.9 |
| Regime (young age group) | 8 | 13.75 | 20.63 | 6.88 |
| Regime (middle age group) | 12 | 15.67 | 22.08 | 6.41 |

$^a$in days

We claim:

1. A method of increasing the rate of skin cell turnover without causing skin irritation which comprises applying to the skin in a regime:

(a) a cleanser formulation consisting essentially of, in percent by weight:

| Ingredients | Percent |
|---|---|
| deionized water | 39.73 |
| propylene glycol | 6.00 |
| magnesium aluminum silicate | 1.10 |
| sodium carboxymethyl cellulose | 0.10 |
| methyl p-hydroxybenzoate | 0.20 |
| imidazolidinyl urea | 0.30 |
| ethylenediaminetetraacetic acid | 0.02 |
| sodium N-lauryl-&-iminodipropionate | 4.00 |
| titanium dioxide | 0.75 |
| sodium isostearoyl-2-lactylate | 2.00 |
| soya sterols | 1.00 |
| polyoxyethylene (10) soya sterols | 2.50 |
| polyoxyethylene (3) myristyl ether myristate | 8.00 |
| polyoxypropylene (15) stearyl ether | 8.00 |
| heavy mineral oil | 8.00 |
| propylene glycol dicaprylate/dicaprate (80/20 to 50/50) | 7.00 |
| cetyl alcohol (1-hexadecanol) | 4.00 |
| stearyl alcohol (1-octadecanol) | 2.00 |
| propyl p-hydroxybenzoate | 0.10 |
| glyceryl monostearate and polyethylene glycol (100) monostearate | 2.00 |
| triple pressed stearic acid | 2.50 |
| lactic acid | 1.10 |
| fragrance | 0.60 |

(b) a cream formulation consisting essentially of, in percent by weight:

| Ingredients | Percent |
|---|---|
| light mineral oil | 4.45 |
| polyethylene homopolymer (1500 m. wt., density 0.91 g/cc) | 2.50 |
| undecanoic triglyceride | 2.00 |
| squalane | 5.00 |
| distilled lanolin alcohol | 0.55 |
| white beeswax | 1.00 |
| polydimethyl cyclosiloxane | 9.00 |
| triglyceryl diisostearate | 4.00 |
| isopropyl myristate | 5.00 |
| propyl p-hydroxybenzoate | 0.10 |
| quaternary bentonite | 0.40 |
| deionized water | 59.00 |
| methyl p-hydroxybenzoate | 0.20 |
| 70% sorbitol solution | 5.00 |
| imidazolidinyl urea | 0.30 |
| urea | 0.50 |
| glyoxyldiureide | 0.20 |
| DL-pantothenyl alcohol | 0.50 |
| cis-1-(3-chloroallyl)-3,5,7-triaza-1-azoniaadamantane chloride | 0.10 |
| fragrance | 0.20 |

(c) a lotion formulation consisting essentially of, in percent by weight:

| Ingredients | Percent |
|---|---|
| deionized water | 69.35 |
| xanthan gum | 0.15 |
| propylene glycol | 5.00 |
| polyoxyethylene (30) stearate | 1.70 |
| methyl p-hydroxybenzoate | 0.20 |
| imidazolidinyl urea | 0.30 |
| polyphenylmethylsiloxane | 3.00 |
| polyethylene homopolymer (1500 m. wt., density 0.91 g/cc) | 1.00 |
| glyceryl monostearate, neutral non-emulsifying | 2.00 |
| propyl p-hydroxybenzoate | 0.20 |
| sorbitan monostearate | 2.00 |
| ethylene glycol monostearate | 1.00 |
| lanolin oil | 2.50 |
| isopropyl myristate | 3.00 |
| squalane | 8.50 |
| fragrance | 0.10 |

(d) a tonic formulation consisting essentially of, in percent by weight:

| Ingredients | Percent |
|---|---|
| deionized water | 80.12 |
| polyethylene and polypropylene glycol | 2.00 |
| glyoxyldiureide | 0.20 |
| polyethylene glycol (300) | 9.00 |
| imidazolidinyl urea | 0.40 |
| denatured alcohol | 7.00 |
| methyl p-hydroxybenzoate | 0.10 |
| propyl p-hydroxybenzoate | 0.05 |
| polyoxyethylene (60) sorbitan fatty acid ester | 0.30 |
| polyoxyethylene (10) oleylether | 0.50 |
| menthol | 0.03 |
| fragrance | 0.30 |

2. The method of claim 1 wherein the tonic is used in the morning, followed by the lotion and later, at night, the cleanser, the tonic, and the cream are applied.

* * * * *

UNITED STATES PATENT AND TRADEMARK OFFICE
CERTIFICATE OF CORRECTION

PATENT NO. : 4,272,544
DATED : June 9, 1981
INVENTOR(S) : John A. Cella et al.

It is certified that error appears in the above-identified patent and that said Letters Patent are hereby corrected as shown below:

In Claim 1, column 7, line 68, across from lactic acid, "1.10" should read -- 0.10 --.

Signed and Sealed this

Twenty-fourth Day of November 1981

[SEAL]

Attest:

GERALD J. MOSSINGHOFF

*Attesting Officer*   *Commissioner of Patents and Trademarks*